(12) United States Patent
Daly et al.

(10) Patent No.: US 11,166,661 B2
(45) Date of Patent: Nov. 9, 2021

(54) INTRA VAGINAL DEVICE TO AID IN TRAINING AND DETERMINING MUSCLE STRENGTH

(75) Inventors: Geoffrey Daniel Daly, Sherwood (AU); Chelsea Cornelius, Middle Park (AU)

(73) Assignee: Analytica Limited, Queensland (AU)

( * ) Notice: Subject to any disclaimer, the term of this patent is extended or adjusted under 35 U.S.C. 154(b) by 0 days.

(21) Appl. No.: 14/112,855

(22) PCT Filed: Jan. 9, 2012

(86) PCT No.: PCT/AU2012/000012
§ 371 (c)(1),
(2), (4) Date: Nov. 12, 2013

(87) PCT Pub. No.: WO2012/142646
PCT Pub. Date: Oct. 26, 2012

(65) Prior Publication Data
US 2014/0066813 A1    Mar. 6, 2014

(30) Foreign Application Priority Data

Apr. 19, 2011    (AU) .................................. 2011901469

(51) Int. Cl.
*A61B 5/22*    (2006.01)
*A61B 5/00*    (2006.01)
(Continued)

(52) U.S. Cl.
CPC .............. *A61B 5/227* (2013.01); *A61B 5/036* (2013.01); *A61B 5/4337* (2013.01);
(Continued)

(58) Field of Classification Search
CPC ....... A61B 5/036; A61B 5/227; A61B 5/4337; A63B 23/20
See application file for complete search history.

(56) References Cited

U.S. PATENT DOCUMENTS 1,704,000 A  *  3/1929  Herwig et al. ................ 607/138
3,933,147 A  *  1/1976  Du Vail ............... A61N 1/0512
                                                    600/591
(Continued)

FOREIGN PATENT DOCUMENTS

AU          739990          10/2001
AU          780359           3/2005
(Continued)

OTHER PUBLICATIONS

PCT/AU2012/000012 Search Report for EP12774420 dated Aug. 5, 2014.
(Continued)

*Primary Examiner* — Sean P Dougherty
*Assistant Examiner* — Benjamin S Melhus
(74) *Attorney, Agent, or Firm* — Fitch, Even, Tabin & Flannery LLP

(57) ABSTRACT

An intra vaginal device (10) including an elongated hollow body (11) with side wall portions (15, 16 and 24). Secured to each wall portion (15 and 24) is a sensor (19), while secured to the wall portion (16) is a sensor (20). The sensors (19) simply measure forces directly applied by the bi-lateral contraction of the pubococcygeus, while the sensor (20) provides an indication of the puborectalis contraction forces.

23 Claims, 2 Drawing Sheets

(51) Int. Cl.
  *A61B 5/03* (2006.01)
  *A63B 23/20* (2006.01)
  *A63B 21/002* (2006.01)
(52) U.S. Cl.
  CPC .......... *A63B 21/0023* (2013.01); *A63B 23/20* (2013.01); *A63B 2220/56* (2013.01); *A63B 2220/833* (2013.01); *A63B 2225/50* (2013.01)

(56) References Cited

U.S. PATENT DOCUMENTS

| | | | |
|---|---|---|---|
| 4,396,019 A | | 8/1983 | Perry et al. |
| 4,881,526 A | * | 11/1989 | Johnson ................ A61H 19/44 601/15 |
| 5,154,177 A | * | 10/1992 | Eisman ................ A61B 5/0492 600/373 |
| 5,233,987 A | * | 8/1993 | Fabian ................ A61B 10/00 600/587 |
| 5,370,671 A | * | 12/1994 | Maurer ................ A61N 1/0524 607/138 |
| 5,452,719 A | * | 9/1995 | Eisman ................ A61N 1/0512 600/373 |
| 5,456,709 A | * | 10/1995 | Hamedi ................ A61N 1/0512 607/138 |
| 5,533,515 A | * | 7/1996 | Coller ................ A61B 5/42 600/593 |
| 5,816,248 A | * | 10/1998 | Anderson ............ A61N 1/0524 128/830 |
| 5,865,801 A | * | 2/1999 | Houser ................ A61B 5/036 600/488 |
| D407,157 S | * | 3/1999 | Malewicz ................ D24/141 |
| 5,881,731 A | | 3/1999 | Remes |
| D415,835 S | * | 10/1999 | Malewicz ................ D24/187 |
| 6,110,099 A | * | 8/2000 | Benderev ............ A61F 2/0009 128/DIG. 25 |
| 6,432,037 B1 | * | 8/2002 | Eini ................ A61B 5/04882 128/898 |
| 7,628,744 B2 | * | 12/2009 | Hoffman ............ A61B 5/0002 128/905 |
| 7,699,844 B2 | * | 4/2010 | Utley ................ A61B 18/1485 606/41 |
| 8,369,953 B2 | * | 2/2013 | Peddicord ............ A61H 19/00 607/41 |
| 8,509,900 B2 | * | 8/2013 | Boyd ................ A61N 1/0524 607/41 |
| 8,597,290 B2 | * | 12/2013 | Utley ................ A61B 1/00087 606/41 |
| D710,007 S | | 7/2014 | Cornelius |
| 8,805,509 B2 | * | 8/2014 | Boyd ................ A61N 1/0512 607/41 |
| 8,983,627 B2 | * | 3/2015 | Pelger ................ A61B 5/04882 607/138 |
| 9,724,036 B2 | * | 8/2017 | Broens ................ A61B 5/42 |
| 2003/0083590 A1 | * | 5/2003 | Hochman ............ A61B 5/04 600/549 |
| 2004/0030360 A1 | * | 2/2004 | Eini ................ A61B 5/04882 607/39 |
| 2005/0228316 A1 | | 10/2005 | Morgenstern |
| 2006/0036188 A1 | | 2/2006 | Hoffman et al. |
| 2007/0293792 A1 | * | 12/2007 | Sliwa ................ A61B 5/0051 600/587 |
| 2009/0171144 A1 | | 7/2009 | Squicciarini |
| 2009/0222060 A1 | * | 9/2009 | Boyd ................ A61N 1/36007 607/48 |
| 2010/0106216 A1 | * | 4/2010 | Cha ................ A61N 1/0524 607/41 |
| 2010/0174218 A1 | * | 7/2010 | Shim ................ A61B 5/1107 601/84 |
| 2010/0280309 A1 | * | 11/2010 | von Pechmann ............ A61B 17/00234 600/37 |
| 2011/0196263 A1 | | 8/2011 | Egorov |
| 2012/0265044 A1 | * | 10/2012 | Broens ................ A61N 1/0512 600/373 |
| 2014/0066813 A1 | | 3/2014 | Daly |
| 2015/0032030 A1 | | 1/2015 | Iglesias |

FOREIGN PATENT DOCUMENTS

| | | |
|---|---|---|
| DE | 4134116 | 4/1993 |
| GB | 2492754 | 1/2013 |
| WO | 9220283 | 11/1992 |
| WO | 2012138232 | 10/2012 |
| WO | 2012142646 | 10/2012 |
| WO | 2013116310 | 8/2013 |
| WO | 2015103629 | 7/2015 |
| WO | 2016042310 | 3/2016 |
| WO | 2016067023 | 5/2016 |

OTHER PUBLICATIONS

International Search Report, International Application No. PCT/US2012/000012, dated Feb. 8, 2012, 2 pages.

Intellectual Property India, Examination Report issued in Application No. 8071/DELNP/2013, dated Feb. 12, 2019, 6 pp.

National Institute of Intellectual Property, Search Report issued in Brazilian Application No. BR112013027117-5, dated Sep. 23, 2019, 6 pp.

International Search Report issued in International Application No. PCT/AU2015/000619, dated Nov. 6, 2015, 4 pp.

Nicholas, L., Analytica's PeriCoach offers improvement in incontinence symptoms, https://smallcaps.com.au/analyticas-pericoach-offers-improvement-incontinence-symptoms/, Aug. 21, 2018, 3 pp.

United States Patent and Trademark Office, Final Office Action issued in U.S. Appl. No. 15/533,359, filed Jun. 13, 2019, 12 pp.

United States Patent and Trademark Office, Non-final Office Action issued in U.S. Appl. No. 15/533,359, filed Dec. 31, 2018, 15 pp.

United States Patent and Trademark Office, Non-final Office Action issued in U.S. Appl. No. 15/533,359, filed May 26, 2020, 14 pp.

* cited by examiner

INTRA VAGINAL DEVICE TO AID IN TRAINING AND DETERMINING MUSCLE STRENGTH

CROSS-REFERENCE TO RELATED APPLICATIONS

This application is a national phase application of International Application No. PCT/AU2012/000012, filed Jan. 9, 2012, claiming priority to Australian Provisional Application No. 2011901469, filed Apr. 19, 2011, which is incorporated by reference herein in its entirety.

TECHNICAL FIELD

The present invention relates to intra vaginal devices to aid in determining muscle strength and more particularly but not exclusively to perineometers.

BACKGROUND OF THE INVENTION

The group of muscles involved in performing a kegel exercise (and hence responsible for continence) is the levator ani. Making up part of the levator ani is the pubococcygeus and the puborectalis. The pubococcygeus arises from pubis (pubic bone) and inserts into the lateral part of the coccyx (sides of coccyx) and so when contracted, presses bilaterally against the walls of the vagina. The puborectalis arises from the superior and inferior pubic rami (front part of pelvis, either side of pubis) and forms a sling around the rectum. Hence when contracted, it "pulls forward" to aid in closing off the canals. The strength of both is essential in maintaining continence.

Many perineometers currently available measure the pressure change inside the vaginal canal upon muscle contract. These devices have the disadvantage that they do not give any indication of the muscle movement or actual contraction force. It may also lead to deterioration of a patient's condition if they are in fact performing the contraction incorrectly—the problem being that "bearing down" using the stomach muscles can also increase the pressure inside the vaginal canal, thus giving an incorrect indication of muscle contraction.

Known perineometers are described in Australian Patent 739990, Australian Patent 780359 and International Patent Publication WO 92/20283.

OBJECT OF THE INVENTION

It is the object of the present invention to overcome or substantially ameliorate the above disadvantage.

SUMMARY OF THE INVENTION

There is disclosed herein an intra vaginal device to aid in determining muscle strength, said device including:

an elongated body having an end portion, a base spaced from the end portion, and a longitudinally extending side wall extending between the end portion and the base;

a first sensor, the sensor being mounted on the side wall and to provide an indication of pressure applied thereto; and a second sensor, the second sensor being mounted on the side wall so as to be spaced angularly about said axis from the second sensor, and to provide an indication of the pressure applied to the second sensor.

Preferably, said end portion is convex.

Preferably, said side wall includes a first side wall portion to which the first sensor is attached, and a second side wall portion to which the second sensor is attached, with the second sensor being angularly displaced about said axis from the first sensor by approximately 80° to 90°.

Preferably, said side wall includes a third side wall portion, and the device further includes a third sensor attached to the third side wall portion, with the third sensor being spaced angularly about said axis from the first and second sensors.

Preferably, the third sensor is spaced approximately 80° to 90° from the first sensor.

Preferably, the wall portions are generally planar.

In an alternative preferred form, the wall portions are convex.

Preferably, at least one of the sensors provides an electrical resistance that diminishes with an increase of pressure applied thereto.

Preferably, the sensors are elongated longitudinally of said body.

Preferably, said base is elongated in a direction transverse of said direction.

Preferably, said base is adapted to engage the vaginal entrance to aid in correctly locating the sensors.

BRIEF DESCRIPTION OF THE DRAWINGS

A preferred form of the present invention will now be described by way of example with reference to the accompanying drawings wherein.

DETAILED DESCRIPTION OF THE PREFERRED EMBODIMENT

Figure 1:
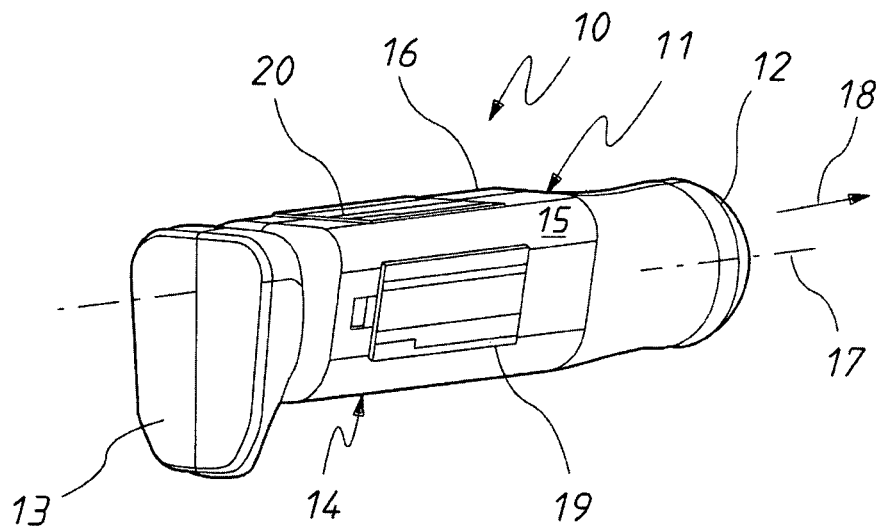
FIG. 1 is a schematic isometric view of a intra vaginal device to aid in measuring muscle strength.
Figures 2, 3:
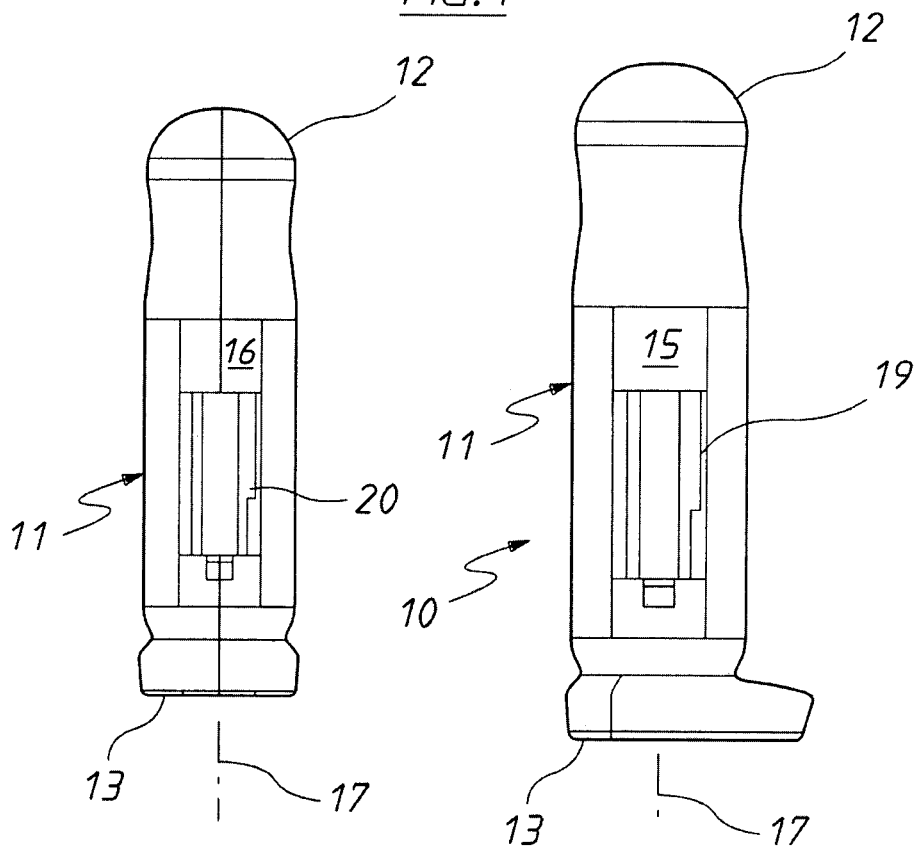
FIG. 2 is a schematic top plan view of the device of FIG. 1.
FIG. 3 is a schematic side elevation of the device of FIG. 1.
Figure 4:
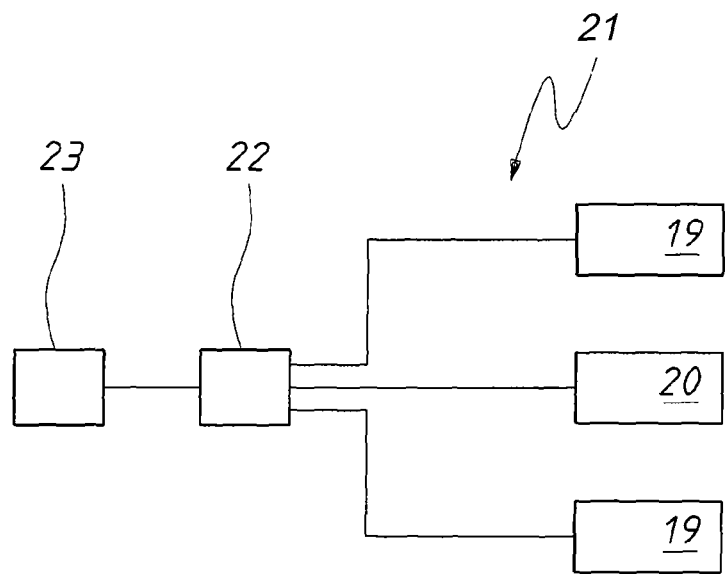
FIG. 4 is a schematic diagram of an electronic circuit employed in the device of FIG. 1.
Figure 5:
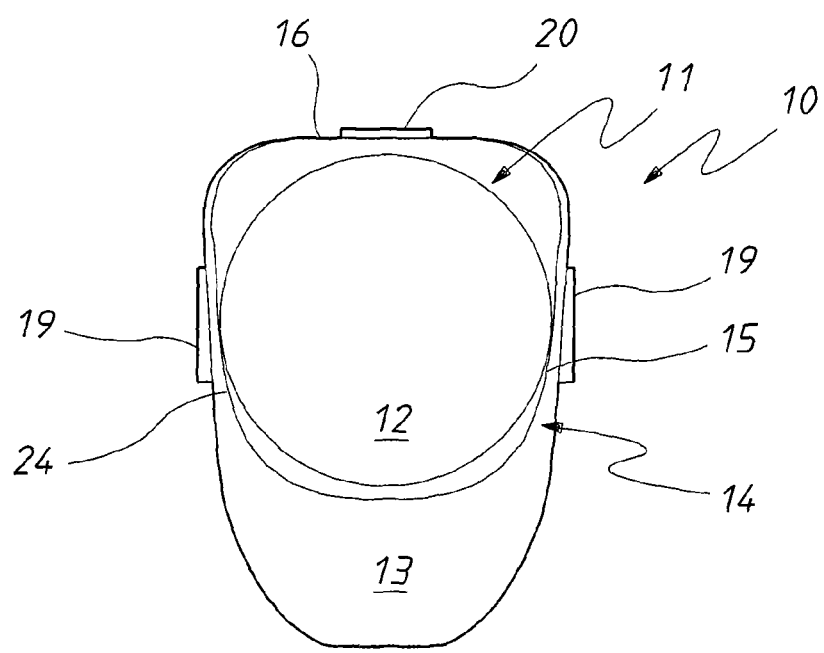
FIG. 5 is a schematic end elevation of the device of FIG. 1.1

In the accompanying drawings there is schematically depicted a device 10 to be inserted in a woman's vagina to aid in measuring muscles operatively associated with the women's vagina.

The device 10 includes an elongated hollow body 11 having an end portion 12, a base 13 and a longitudinally extending side wall 14. The side wall 14 includes side wall portions 15, 16 and 24. Preferably, the side wall portions 15, 16 and 24 are generally planar (or convex) and the portion 12 generally convex.

The device 10 has a longitudinal axis 17.

Secured to each wall portion 15 and 24 is a sensor 19, while secured to the wall portion 16 is a sensor 20. Each of the sensors 19 and 20 is adapted to provide an indication of the pressure applied thereto. As a particular example, the sensors 19 and 20 could provide an electrical resistance that increases or decreases with pressure applied thereto, preferably decreases.

Preferably, the sensor 20 is spaced angularly about the axis 17 by an angle of approximately 80° to 90° from each of the sensors 19.

Preferably, the sensors 19 are spaced from the base 13 by the said distance. The sensor 20 is placed at a desired distance from the base 13, that may be the same or smaller distance from the base 13 than the sensors 19. Preferably, the sensors 19 and 20 are elongated longitudinally relative to the body 11.

Preferably, the base 13 is transversely elongated to aid a user to manipulate the device 10 and to aid in correctly positioning the device 10 by having the base 13 engage the vaginal entrance.

Preferably, the device 10 includes an electronic circuit 21 incorporating the sensors 19 and 20. The circuit 21 includes a processor 22 that interrogates the sensors 19 and 20 to determine their resistance, and then to provide a signal for a read out 23 that provides information in respect of the muscles associated with the user's vagina. The read out 23 may be remote from body 11 and communicates via wireless with the processor 22.

The sensor 20 provides an indication of the puborectalis contraction forces, the sensors 19 provide an indication of the pressure applied by the pubococcygeus.

The device 10 is shaped in such a way that once inserted into the vagina, it is able to measure both modes of contraction. The device 10 is inserted in the direction 18. The sensor 20 is preferably on top of the device 10 and measures the force applied to the device 10 by the urethral wall—thus capturing the contraction strength contributed by the puborectalis.

The sensors 19 are on the sides of the device 10.

The base 13 is spaced from the sensors 19 and 20 so that the base 13 upon engaging the entrance of the vagina, correctly locates the sensors 19 and 20.

The sensors 19 are able to separately measure the force directly applied by the bilateral contraction of the pubococcygeus.

The force measurements can also be combined to give an average contraction strength output.

This separation of the measurements enables a more thorough understanding of the overall contraction and may lead to easier diagnosis of incontinence problems, as well as an invaluable teaching aide. There are many factors involved in incontinence, and this may enable clinicians to identify the muscle group that is contributing to incontinence in different case studies.

This specific feedback is also essential in encouraging and maintaining consistency with patients using the device.

This ability to distinguish between the specific muscles and modes of contraction may also be helpful in addressing a common issue of over-clenching of the pelvic floor. Many women suffer from this condition and need to be taught how to relax these muscles. The device 10 would be able to offer a more accurate picture of the clenching problem by measuring the full input of each muscle, and possibly pinpointing which area to focus on.

Preferably in use of the device 10, the device 10 is covered by a sheath. As a particular example, the sheath may be of a synthetic rubber.

The invention claimed is:

1. An intra vaginal device to be inserted through a vaginal opening to aid in determining muscle strength, said device including:
   an elongated body having a longitudinal axis, an end portion, a base spaced from the end portion, and a longitudinally extending side wall extending between the end portion and the base;
   a first sensor, the first sensor being mounted on the side wall and providing an indication of pressure applied thereto by puborectalis contractions of the patient; and
   a second sensor, the second sensor being mounted on the side wall so as to be spaced angularly about said longitudinal axis from the first sensor, and providing an indication of the pressure applied to the second sensor by the patient's pubococcygeus;
   wherein said side wall includes a first side wall portion to which the first sensor is attached, and a second side wall portion to which the second sensor is attached, with the second sensor being angularly displaced about said longitudinal axis from the first sensor by 80° to 90°, and the base is elongated in a direction transverse of said longitudinal axis so as to have a length greater than a width transverse of said longitudinal axis to aid a user to manipulate the device and to aid in correctly positioning the device by having the base engage the vaginal entrance so that a first sensor pressure is applied to the first sensor by the puborectalis contractions and a second sensor pressure is applied to the second sensor by the pubococcygeus, with the device providing a user with separate measurements of the first sensor pressure and second sensor pressure; and
   wherein the body transitions from a rounded front portion to a non-rounded intermediate portion where the sensors are located; and wherein the intermediate portion is trapezoidal in cross-section in a direction transverse of said longitudinal axis.

2. The device of claim 1, wherein said end portion is convex.

3. The device of claim 2, wherein said side wall includes a third side wall portion, the device further includes a third sensor attached to the third side wall portion, with the third sensor being spaced angularly about said longitudinal axis from the first and second sensors, and the third sensor is spaced 80° to 90° from the first sensor so as to provide an indication of the pressure applied by the patient's pubococcygeus.

4. The device of claim 3, wherein the side wall portions are planar.

5. The device of claim 3, wherein the side wall portions are convex.

6. The device of claim 3, wherein at least one of the sensors provides an electrical resistance that diminishes with an increase of pressure applied thereto.

7. The device of claim 3, wherein the sensors are elongated longitudinally of said body.

8. The device of claim 3, wherein at least one of the sensors provides an electrical resistance that diminishes with an increase of pressure applied thereto, the sensors are elongated longitudinally of said body, said base is elongated in a direction transverse of the side wall and is adapted to engage the vaginal entrance to aid in correctly locating the sensors.

9. The device of claim 1, wherein said side wall includes a third side wall portion, and the device further includes a third sensor attached to the third side wall portion, with the third sensor being spaced angularly about said longitudinal axis from the first and second sensors.

10. The device of claim 9, wherein the third sensor is spaced 80° to 90° about said longitudinal axis from the first sensor so as to provide an indication of the pressure applied by the patient's pubococcygeus.

11. The device of claim 1, wherein the side wall portions are planar.

12. The device of claim 1, wherein the side wall portions are convex.

13. The device of claim 1, wherein at least one of the sensors provides an electrical resistance that diminishes with an increase of pressure applied thereto.

14. The device of claim 1, wherein the sensors are elongated longitudinally of said body.

15. The device of claim 1, wherein the base extends from the first side wall portion transversely across said longitudinal axis so as to extend from said first side wall portion away from said first side wall portion.

16. The intra vaginal device of claim 1 wherein the circular front portion is smaller than the non-circular intermediate portion in cross-section in a direction transverse of said longitudinal axis, and wherein the intermediate portion is smaller than the base in cross-section in a direction transverse of said longitudinal axis.

17. The intra vaginal device of claim 1 wherein the first and second sensors are parallel, and wherein the side wall portions from which the first and second sensors extend are non-parallel.

18. The intra vaginal device of claim 1 further comprising a recessed portion between the base and the intermediate portion.

19. The intra vaginal device of claim 1 wherein the base is trapezoidal in a direction transverse of said longitudinal axis, having two generally parallel side edges and two generally non-parallel side edges.

20. An intra vaginal device to be inserted through a vaginal opening to aid in determining muscle strength, said device including:
    an elongated body having a longitudinal axis, an end portion, a base spaced from the end portion, and a longitudinally extending side wall extending between the end portion and the base;
    a first sensor, the first sensor being mounted on the side wall and providing an indication of pressure applied thereto by puborectalis contractions of the patient; and
    a second sensor, the second sensor being mounted on the side wall so as to be spaced angularly about said longitudinal axis from the first sensor, and providing an indication of the pressure applied to the second sensor by the patient's pubococcygeus;
    wherein said side wall includes a first side wall portion to which the first sensor is attached, and a second side wall portion to which the second sensor is attached, with the second sensor being angularly displaced about said longitudinal axis from the first sensor by 80° to 90°, and the base is elongated in a direction transverse of said longitudinal axis so as to have a length greater than a width transverse of said longitudinal axis to aid a user to manipulate the device and to aid in correctly positioning the device by having the base engage the vaginal entrance so that a first sensor pressure is applied to the first sensor by the puborectalis contractions in a direction parallel to the length of the base and a second sensor pressure is applied to the second sensor by the pubococcygeus, with the device providing a user with separate measurements of the first sensor pressure and second sensor pressure; and
    wherein the side wall portions are generally or substantially flat, and wherein the side wall portions are non-circular in cross-section and generally form a trapezoidal shape having a pair of parallel sides and a pair of non-parallel sides.

21. An intra vaginal device to be inserted through a vaginal opening to aid in determining muscle strength, said device including:
    an elongated body having a longitudinal axis, an end portion, a base spaced from the end portion, and a longitudinally extending side wall extending between the end portion and the base;
    a first sensor, the first sensor being mounted on the side wall and providing an indication of pressure applied thereto by puborectalis contractions of the patient; and
    a second sensor, the second sensor being mounted on the side wall so as to be spaced angularly about said longitudinal axis from the first sensor, and providing an indication of the pressure applied to the second sensor by the patient's pubococcygeus;
    wherein said side wall includes a first side wall portion to which the first sensor is attached, and a second side wall portion to which the second sensor is attached, with the second sensor being angularly displaced about said longitudinal axis from the first sensor by 80° to 90°, and the base is elongated in a direction transverse of said longitudinal axis so as to have a length greater than a width transverse of said longitudinal axis to aid a user to manipulate the device and to aid in correctly positioning the device by having the base engage the vaginal entrance so that a first sensor pressure is applied to the first sensor by the puborectalis contractions in a direction parallel to the length of the base and a second sensor pressure is applied to the second sensor by the pubococcygeus, with the device providing a user with separate measurements of the first sensor pressure and second sensor pressure; and
    wherein the side wall includes a plurality of side wall portions including the first side wall portion and the second side wall portion, and wherein the second side wall portion is adjacent to and substantially transverse to the first side wall portion, and wherein the side wall portions are non-circular in cross-section and generally form a trapezoidal shape having a pair of parallel sides and a pair of non-parallel sides.

22. The device of claim 21, wherein the first sensor being located on one of the parallel sides and the second sensor being located on one of the non-parallel sides adjacent the parallel side having the first sensor.

23. The device of claim 22, wherein the second sensor comprises two sensors located on opposite non-parallel sides adjacent the parallel side having the first sensor.

* * * * *

UNITED STATES PATENT AND TRADEMARK OFFICE
CERTIFICATE OF CORRECTION

PATENT NO. : 11,166,661 B2  
APPLICATION NO. : 14/112855  
DATED : November 9, 2021  
INVENTOR(S) : Geoffrey Daniel Daly et al.

Page 1 of 1

It is certified that error appears in the above-identified patent and that said Letters Patent is hereby corrected as shown below:

On the Title Page

Under References Cited,  
U.S. PATENT DOCUMENTS,  
Column 2, Line 2: 3,933,147 A * 1/1976 Du Vail .......... A61N 1/0512  
Change "Vail" to -- Vall --.

Signed and Sealed this  
Twenty-fifth Day of January, 2022

Drew Hirshfeld  
*Performing the Functions and Duties of the*  
*Under Secretary of Commerce for Intellectual Property and*  
*Director of the United States Patent and Trademark Office*